US009603686B2

(12) United States Patent
Schaefer et al.

(10) Patent No.: US 9,603,686 B2
(45) Date of Patent: Mar. 28, 2017

(54) ORAL HYGIENE IMPLEMENT (71) Applicant: Braun GmbH, Kronberg (DE)

(72) Inventors: Norbert Schaefer, Frankfurt am Main (DE); Thomas Fritsch, Eppstein (DE); Joern Utsch, Eschborn (DE); Wolfgang Stegmann, Frankfurt am Main (DE)

(73) Assignee: BRAUN GMBH, Kronberg (DE)

( * ) Notice: Subject to any disclaimer, the term of this patent is extended or adjusted under 35 U.S.C. 154(b) by 97 days.

(21) Appl. No.: 14/333,776

(22) Filed: Jul. 17, 2014

(65) Prior Publication Data
US 2015/0020324 A1 Jan. 22, 2015

(30) Foreign Application Priority Data

Jul. 17, 2013 (EP) ..................... 13176787

(51) Int. Cl.
A61C 17/22 (2006.01)
A61C 17/34 (2006.01)
B29C 45/26 (2006.01)
A46B 5/00 (2006.01)

(52) U.S. Cl.
CPC .......... *A61C 17/222* (2013.01); *A46B 5/0095* (2013.01); *A61C 17/3436* (2013.01); *B29C 45/261* (2013.01); *B29C 45/2628* (2013.01)

(58) Field of Classification Search
CPC ..... A61C 17/005; A61C 17/22; A61C 17/222; A61C 17/24; A61C 17/26
USPC .................................. 15/110, 111
See application file for complete search history.

(56) References Cited

U.S. PATENT DOCUMENTS

| 4,253,832 | A | | 3/1981 | Bailey | |
|---|---|---|---|---|---|
| 4,604,058 | A | | 8/1986 | Fisher et al. | |
| 5,732,432 | A | * | 3/1998 | Hui | A61C 17/16 15/22.1 |
| 5,772,436 | A | | 6/1998 | Matsui et al. | |
| 8,032,967 | B2 | * | 10/2011 | Jimenez | A61C 17/349 15/110 |
| 2002/0066147 | A1 | | 6/2002 | Schutz | |
| 2009/0044357 | A1 | * | 2/2009 | Chan | A61C 17/222 15/110 |

OTHER PUBLICATIONS

European Search Report dated Nov. 20, 2013.

* cited by examiner

*Primary Examiner* — Laura C Guidotti (57) ABSTRACT

The present disclosure is concerned with an oral hygiene implement having a neck section extending along a longitudinal direction and having a neck section housing surrounding a neck section cavity, a head section having a through hole therein extending through the head section along a through hole direction having an angle with respect to the longitudinal direction and having a head section housing surrounding the through hole, wherein the through hole defines a first and a second opening in the head section housing, and wherein a cap element separately made from the head section housing is connected with the head section housing to essentially cover the first opening and a carrier element separately made from the head section housing is arranged to cover the second opening.

15 Claims, 9 Drawing Sheets

ORAL HYGIENE IMPLEMENT

FIELD OF THE INVENTION

The present invention is concerned with an oral hygiene implement having a head section and a neck section. It is further concerned with an oral hygiene device comprising such an oral hygiene implement and with a method of manufacturing an oral hygiene implement.

BACKGROUND OF THE INVENTION

It is known that movably mounted carrier elements of oral hygiene implements (e.g. brush heads) are locked against being removed from a housing of the oral hygiene implement by one or several locking pins. A locking pin represents an additional element that needs to be assembled and the locking pin is also made from metal rather than plastic and thus is relatively costly.

It is an object of the present disclosure to provide an oral hygiene implement and a method for manufacturing an oral hygiene implement that are improved over the known oral hygiene implements or their methods of manufacture.

SUMMARY OF THE INVENTION

In accordance with at least one aspect there is provided an oral hygiene implement comprising a neck section extending along a longitudinal direction and having a neck section housing surrounding a neck section cavity, a head section having a through hole therein extending through the head section along a through hole direction having an angle with respect to the longitudinal direction and having a head section housing surrounding the through hole, wherein the through hole defines a first and a second opening in the head section housing, and wherein a cap element separately made from the head section housing is connected with the head section housing to essentially cover the first opening and a carrier element separately made from the head section housing is arranged to cover the second opening.

In accordance with at least one aspect there is provided an oral hygiene device comprising such an oral hygiene implement.

In accordance with at least one aspect there is provided a method of manufacturing an oral hygiene implement comprising a neck section having a neck section cavity and a neck section housing and a head section having a through hole and a head section housing, the method comprising the steps providing a first mold plate defining at least parts of the outer side of the neck section housing and of the head section housing, the first mold plate comprising at least a first shaping projection, providing a second mold plate defining at least parts of the outer side of the neck section housing and of the head section housing, the second mold plate comprising at least a second shaping projection, providing a core defining at least parts of the inner side of the neck section housing and of the head section housing, the core comprising a shaping front portion, moving the first mold plate, the second mold plate, and the core together so that the first shaping projection, the second shaping projection and the shaping front portion define the inner side of a through hole through the head section housing having a first opening and a second opening, wherein the shaping front portion defines at least a portion of the inner side of the head section housing distal to the neck section, and injecting a plastic material into the mold cavity.

BRIEF DESCRIPTION OF THE DRAWINGS

The present disclosure will be further deepened by a detailed discussion of general and specific embodiments of oral hygiene implements and their manufacturing methods. The further description will refer to figures. In the figures

DETAILED DESCRIPTION OF THE INVENTION

An oral hygiene implement as proposed has a head section housing having a through hole defining a first and a second opening in the head section housing, where the first opening is essentially covered by a cap element and the second opening is essentially covered by a carrier element. The term "essentially" shall mean that the respective opening is not completely covered, as, e.g., a gap may remain between the cap element or the carrier element and the respective opening. In accordance with the present disclosure, the cap element is made separately from the head section housing and the neck housing (the head section housing and the neck section housing may in particular be made as an integral housing). The carrier element may also be made separately from the head section housing and the neck section housing. The cap element may be made as a separate element, e.g. using plastic injection molding, and may then be connected to the head section housing by mechanical coupling means. This connection may in particular happen from the inside of the head section housing, e.g. the cap element may be introduced via the second opening and may then be connected with the head section housing via snap at least one snap hooks and/or by at least one undercut into which a projection extends. Alternatively, the cap element may be directly connected to the head section housing by (plastic) injection molding, where the connection may be established by at least one injection molded fixation element (e.g. a projection extending into a cavity of an inner wall of the head section housing) and/or by chemical bonding between the material of the head section housing and of the cap element. The cap element may additionally or alternatively be fixed or interlocked with respect to the head section housing by at least one additional fixation element. In some embodiments, the fixation element may alternatively or additionally lock the carrier element against being removed from the oral hygiene implement. In some embodiments, the fixation element engages around a projection that extends from an inner wall of the head section housing into the through hole and/or a projection extending from the fixation element engages into a recess provided in the inner wall of the head section housing. In some embodiments, the cap element is made from a different material than the head section housing. In some embodiments, the cap element is textured or has a structure on at least on a part of its outer surface. The cap element may have a circumferential flange to structurally strengthen the cap element. An essentially circumferential gap may extend between a circumferential edge of the cap element and a circumferential edge of the first opening. Such a gap may allow cleaning the through hole with water even after so the first opening is essentially covered by the cap element. In some embodiments, the cap element may have at least one bore allowing liquids to exit the head section cavity.

The through hole allows for making at least one projection that extends from an inner wall of the head section housing into the through hole and allows in particular for making two projections extending from an inner wall of the head section housing and being arranged on top of each other and with a distance with respect to a through hole direction (the through hole direction being defined as a line connecting the centers of mass of the first and second openings) as will be explained in more detail in the following. A through hole as proposed generally allows an improved access to the head section cavity (i.e. the through hole) due to the two opening (in contrast to the single opening that is known in the art so far) and allows making/assembling more complex structures in the head section.

Figure 1:
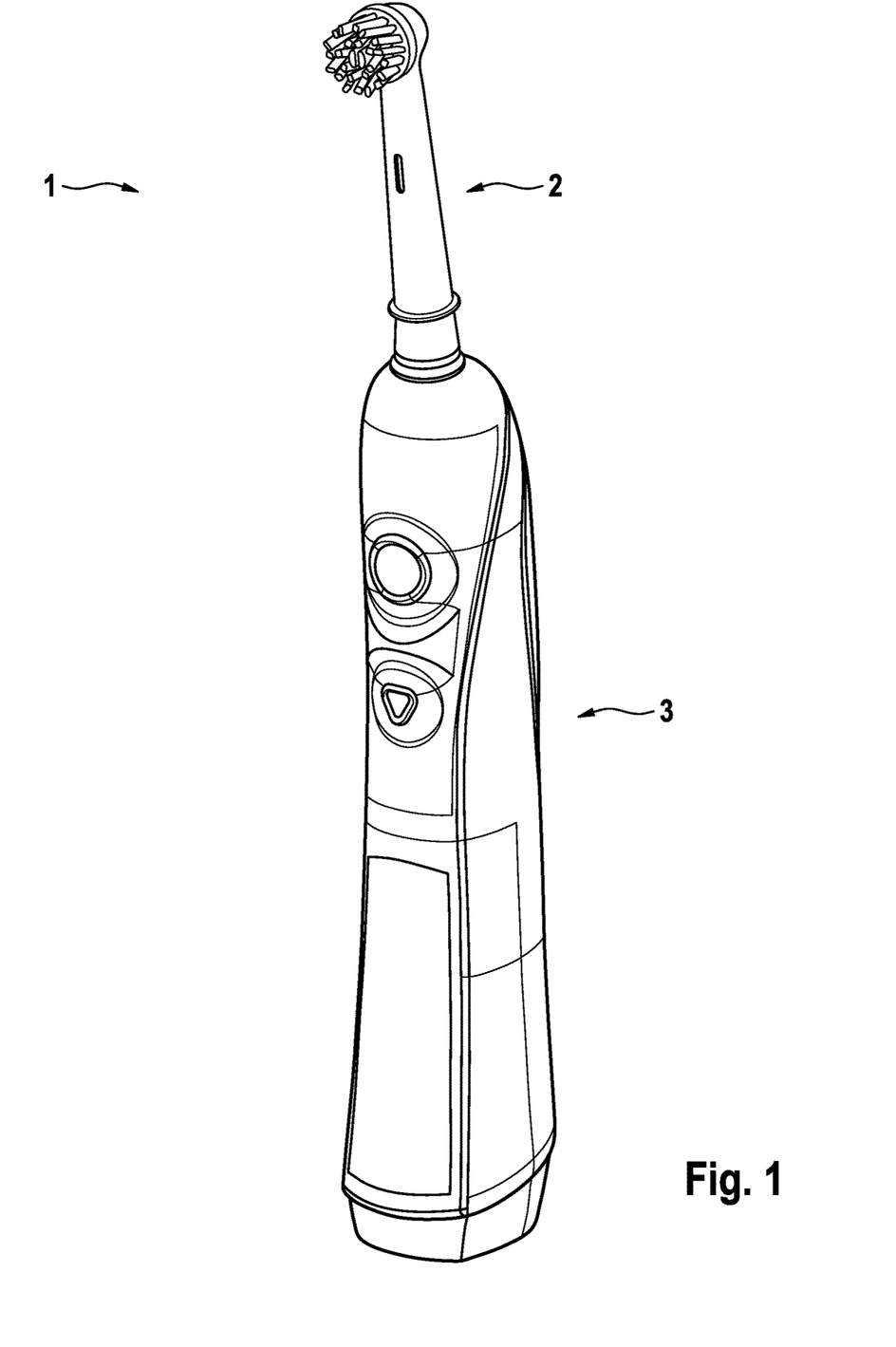
FIG. 1 is a perspective view onto an oral hygiene device comprising an oral hygiene implement and a handle.

FIG. 1 is a depiction of an example embodiment of an oral hygiene device 1 in accordance with the present disclosure. The oral hygiene device 1 comprises an oral hygiene implement 2 and a handle 3. The oral hygiene implement 2 may in particular be detachably attached to the handle 3. While it is shown that the oral hygiene device 1 is realized as a (electric) toothbrush, this shall not be interpreted as limiting. Instead as a toothbrush (e.g. an electric toothbrush), the oral hygiene device may also be realized as a (electric) tongue scraper device, a (electric) gum massage device, a (electric) flossing device etc.

Figure 2:
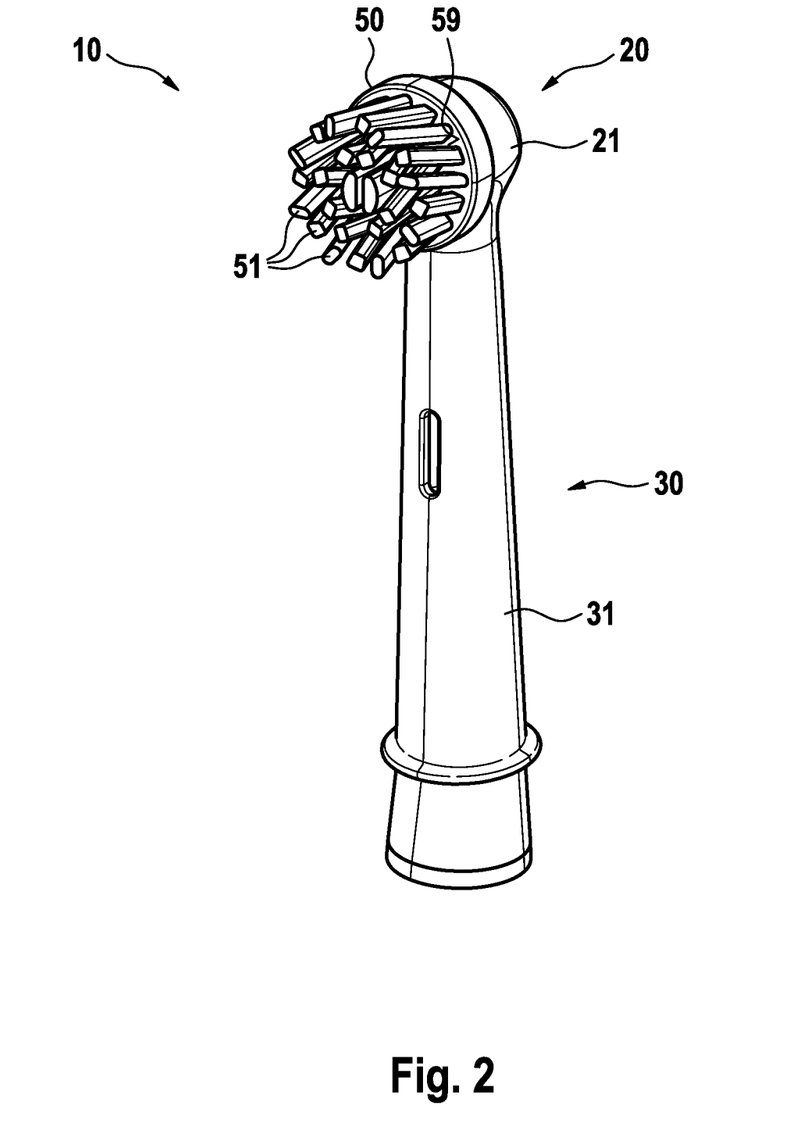
FIG. 2 is a perspective view onto an example embodiment of an oral hygiene implement in accordance with the description.

FIG. 2 is a depiction of an example embodiment of an oral hygiene implement 10 in accordance with the present disclosure, where the oral hygiene implement 10 is shown in a perspective view. The oral hygiene implement 10 comprises a head section 20 having a head section housing 21 and a neck section 30 having a neck section housing 31. As is shown, the head section 20 and the neck section 30 may generally be realized as an integral piece; in particular, the head section 20 and the neck section 30 may have been integrally formed in a (plastic) injection molding process as will be explained in more detail further below. A carrier element 50 may be movably mounted at the head section 10. In the shown example embodiment, the carrier element 50 has a mounting surface 59 on which cleaning elements 51 are mounted, which are intended for cleaning parts of the oral cavity such as the teeth. The carrier element 50 may in particular be movably mounted such that it can be driven into a rotation or oscillatory rotation around a rotation axis (which may be in particular perpendicular to the mounting surface) when attached to a handle of an oral hygiene device.

While it is shown that the oral hygiene implement is realized as a brush head, this shall not be interpreted as limiting. Instead as a brush head, the oral hygiene implement may be realized as a tongue scraper implement, a gum massaging implement, a flossing implement etc.

Figure 3:
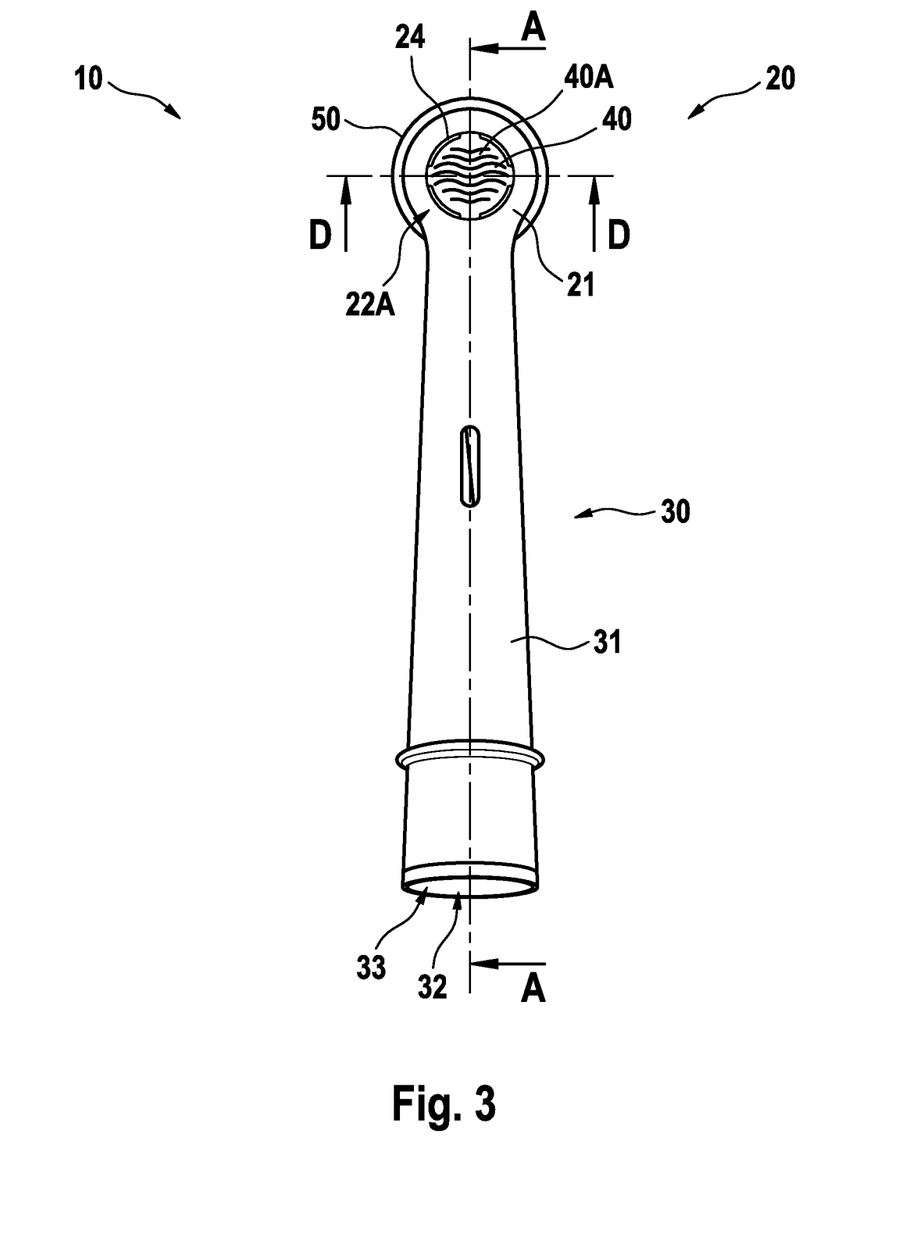
FIG. 3 is a rear view onto the backside of the oral hygiene implement shown in FIG. 2.

FIG. 3 is a depiction of a rear view onto the oral hygiene implement 10 shown in FIG. 2. A cap element 40 is arranged at the back of the head section 20 opposite to the front, where the carrier element 50 is arranged, so that a first opening 22A in the head section 20 is essentially filled (or covered). In some embodiments, a circumferential gap 24 (which extends between the outside and a head section cavity) remains between an edge of the cap element 40 and an edge of the first opening 22A. This circumferential gap 24 allows water and/or saliva or toothpaste to leave (in particular to be rinsed out of) the interior of the head section 20 when the oral hygiene implement 10 is being cleaned with water. In some embodiments, the cap element 40 has an at least partly structured or textured or otherwise enhanced (e.g. printed) outer surface 40A, where this structure, texture or enhancement may have a functional role (such as tongue cleaning capacity) or may just have an aesthetical or informative function. The neck section 30 of the oral hygiene implement 10 has a neck section cavity 33 that is surrounded by the neck section housing 31. The neck section 30 may have an opening 32 at a neck section end opposite to the head section 20.

Figure 4:
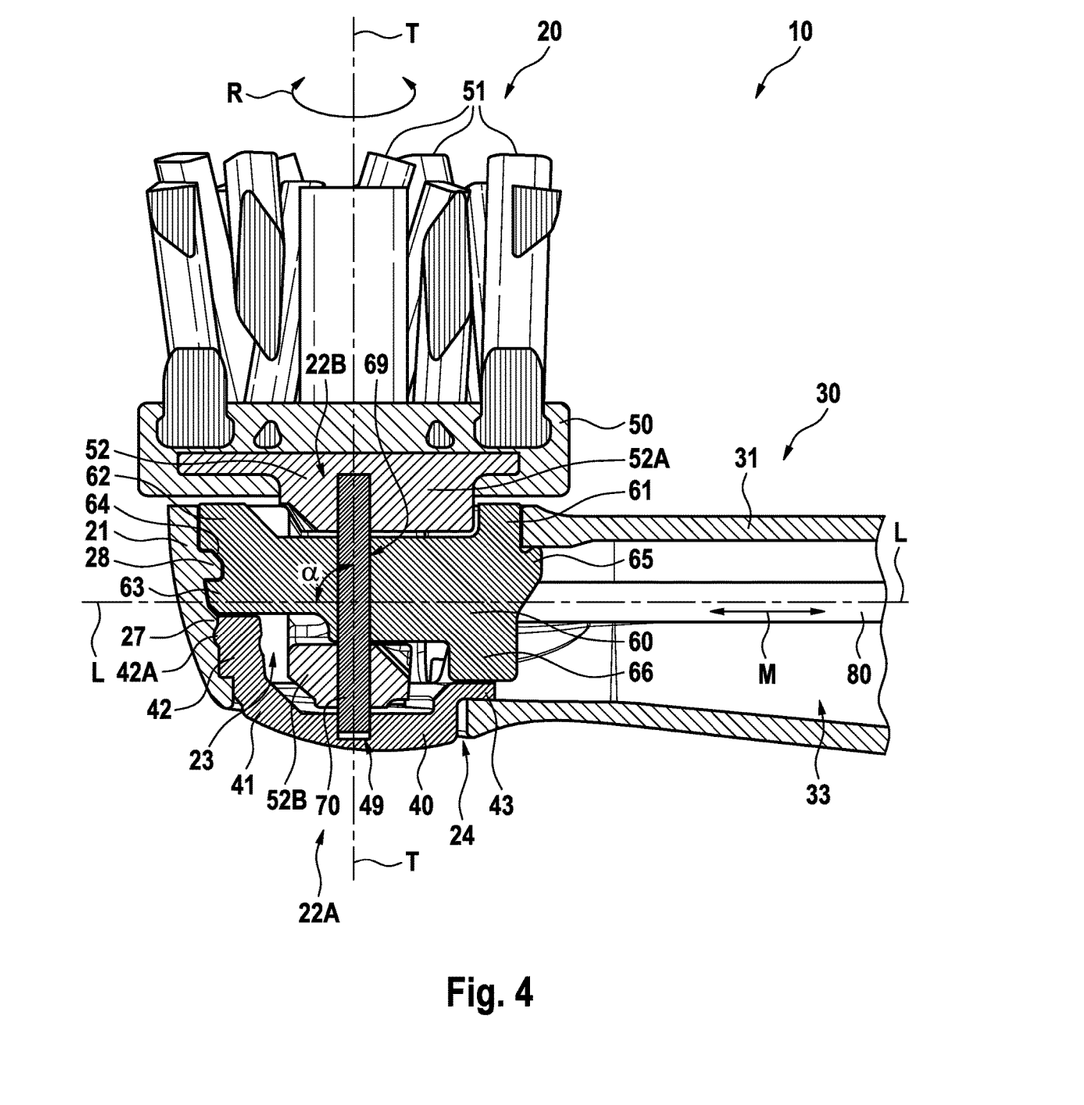
FIG. 4 is a longitudinal cross-sectional cut through the oral hygiene implement shown in FIG. 2 taken through the plane as indicated by line A-A in FIG. 3.

FIG. 4 is a longitudinal cross-sectional cut through the head section 20 and a part of the neck section proximal to the head section 20 of the example oral hygiene implement 10 shown in FIG. 3 along line A-A as indicated in FIG. 3. The neck section housing 31 of the neck section 30 surrounds the neck section cavity 33, which generally extends along a longitudinal direction L. The longitudinal direction L coincides with or at least is parallel to a centre axis of a motion transmitter 80 arranged for transferring motion from a drive shaft of a handle to the carrier element 50 (when the oral hygiene implement 10 is attached to the handle), which centre axis coincides with the motion direction of the motion transmitter 80 indicated by double arrow M. The head section housing 21 of the head section 20 surrounds a through hole 23 that generally extends along a through-hole direction T. The through hole direction T generally has an angle α with respect to the longitudinal direction L, which angle α may in particular be about 90 degrees as is shown, but in general the angle α may have any value, e.g. 5°, 10°, 15°, 20°, 25°, 30°, 35°, 40°, 45°, 50°, 55°, 60°, 65°, 70°, 75°, 80°, 85°, or 90° or any value in-between the given numbers, hence the angle α is in a range of between about 5° to 90°, in particular in a range of about 30° and 90°, further in particular in a range of between 60° to 90°. The through-hole 23 and the neck section cavity 33 together form a connected cavity inside of the oral hygiene implement 10. The trough hole 23 defines a first opening 22A and a second opening 22B in the head section housing 21, which first and second openings 22A and 22B are arranged opposite to each other with respect to the through-hole direction T.

Figure 6:
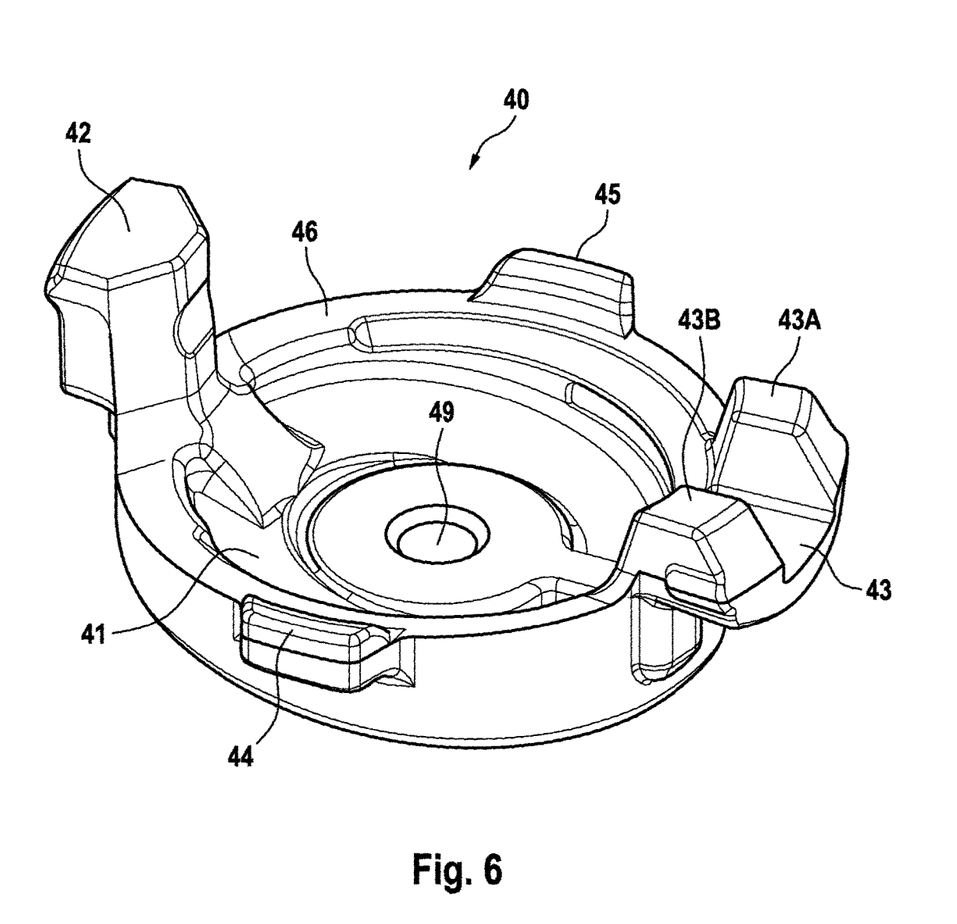
FIG. 6 is a perspective view on an example embodiment of a cap element.

A cap element 40 is arranged at the head section 20 and essentially covers (or fills) the first opening 22A. The cap element 40 may comprise a central cap structure 41 that essentially fills the first opening 22A (a circumferential gap 24 remains between a circumferential edge of the cap structure 41 and an edge of the first opening 22A as was already discussed with respect to FIG. 3). The cap element 40 is here connected to the head section housing 21 from the inside by means of at least one connector structure. In the shown embodiment, a first connector structure 42 has a radially outwards extending projection 42A that is snapped below a first projection 27 of the head section housing 21, which first projection 27 extends from an inner wall of the head section housing 21 radially into the through-hole 23 (here, "radially" is defined with respect to the through-hole direction T). The provision of the projection 42A and of the first projection 27 may fix the cap element 40 at the head section housing 21 in a mounting process, when the cap element 40 may be moved generally from the second opening 22B towards the first opening 22A so that the probability that the cap element 40 loosens in the further mounting steps by which the shown oral hygiene implement 10 may be assembled is reduced. A second connector structure 43 may be clamped in between two lateral wall segments of the head section housing 21 to improve the fixation of the cap element 40. With further reference to FIG. 6, the cap element 40 may have a third connector structure 44 and additionally a fourth connector structure 45 that may both cooperate with respective fixation structures provided in the inner wall of the head section housing 21 to further improve fixation of the cap element 40 in its mounting position. The cap element 40 may have a support structure 49 for supporting and optionally also clamping an axle 70 around which the carrier element 50 is movably mounted.

Generally, the cap element 40 and the carrier element 50 are separately made from the head section housing and/or the neck section housing. The cap element 40 and the carrier element 50 may each be made in individual injection molding procedures. Instead of being provided as a separate element to be assembled, in some embodiments, the cap element may be directly injection molded at the head section housing in a mold different to the mold in which the head section housing was molded.

A fixation element 60 may also be disposed within the through hole 23 of the head section 20. The fixation element 60 may have a through hole 69 for receiving the axle 70 and optionally for clamping the axle 70. In the shown embodiment, the fixation element 60 has two radially extending projections 62 and 63 and between the two projections a radially inwards extending depression 64. A second projection 28 radially extends from an inner side of the head section housing 21 into the through whole 22 and sits in a form-fit manner in the depression 64. The first and the second projections 62, 63 of the fixation element 60 engage around the second projection 28. The second projection 63 of the fixation element 60 may be somewhat retracted with respect to the first projection 62 of the fixation element 60 so that during assembly, when the fixation element 60 may be moved from the second opening 22B towards the first opening 22A, the fixation element 60 snaps around the second projection 28 of the head section housing 21. Lateral wall elements (depicted in FIG. 7) may be provided at the inner side of the head section housing 21 at the lateral sides of the first and section projections 27 and 28 in order to define the position of the fixation element 60. The lower projection 63 of the fixation element may then sit tightly upon the first connector structure 42 and thus interlocks the cap element 40 with respect to the head section housing 21.

Generally, the fixation element and the cap element may be designed such that the fixation element interlocks the cap element with respect to the head section housing and the shown embodiment is to be interpreted as just one example how to achieve this; in particular, the cap element may not be fixed at the head section housing by any other means than the fixation element, i.e. the cap element may be loosely disposed in the head section housing and may then only be fixed with respect to the head section housing by an interlocking action provided by a fixation element that is connected with the head section housing. Or the cap element may be made by injection molding and the fixation element may the serve as additional locking structure, e.g. in case that the injection molded cap element does at least not sufficiently chemically bound with the head section housing. In some embodiments, the fixation element may be connected with the head section housing by at least one locking pin, e.g. a metal pin that extends through a bore in the head section housing (where it may be assembled by force fitting) and into a (blind) bore or recess in the fixation element (where it may also be assembled by force fitting).

The fixation element 60 may have a further radial projection 65 that extends under a wall portion of the head section housing 21 in order to support fixation of the fixation element 60 at the head section 20. In the shown embodiment, the projection 65 has a ramped geometry in axial direction so that the projection 65 can snap underneath the head section housing 21 during the assembly process when the fixation element 60 is moved from the second opening 22B towards the first opening 22A. The fixation element 60 may also have an axial projection 66 designed so that it is in tight contact with at least a portion of the cap element 40 (here: with the second connector structure 43) for additionally supporting the interlocking of the cap element 40 with respect to the head section housing 21.

The carrier element 50 may be movably mounted on the axle 70 so that the carrier element 50 can be driven into a rotational or oscillatory rotational movement around the axle 70 as is indicated by double arrow R. In the shown example embodiment, the rotation axis coincides with the through-hole direction T. As has been discussed with reference to FIG. 2, the carrier element 50 may have a mounting surface 59 on which cleaning elements 51 may be mounted. In the shown embodiment, the carrier element 50 has a mounting structure 52 that has bores for receiving the axle 70 and that has a cavity 52C (shown in FIG. 5) that is arranged between mounting sections 52A and 52B that may envelope the cavity 52C in transverse direction so that the fixation element 60 is received in the cavity 52C and thus the carrier element 50 is locked against being removed from the head section 20. The carrier element 50 essentially fills or covers the second opening 22B.

Figure 5:
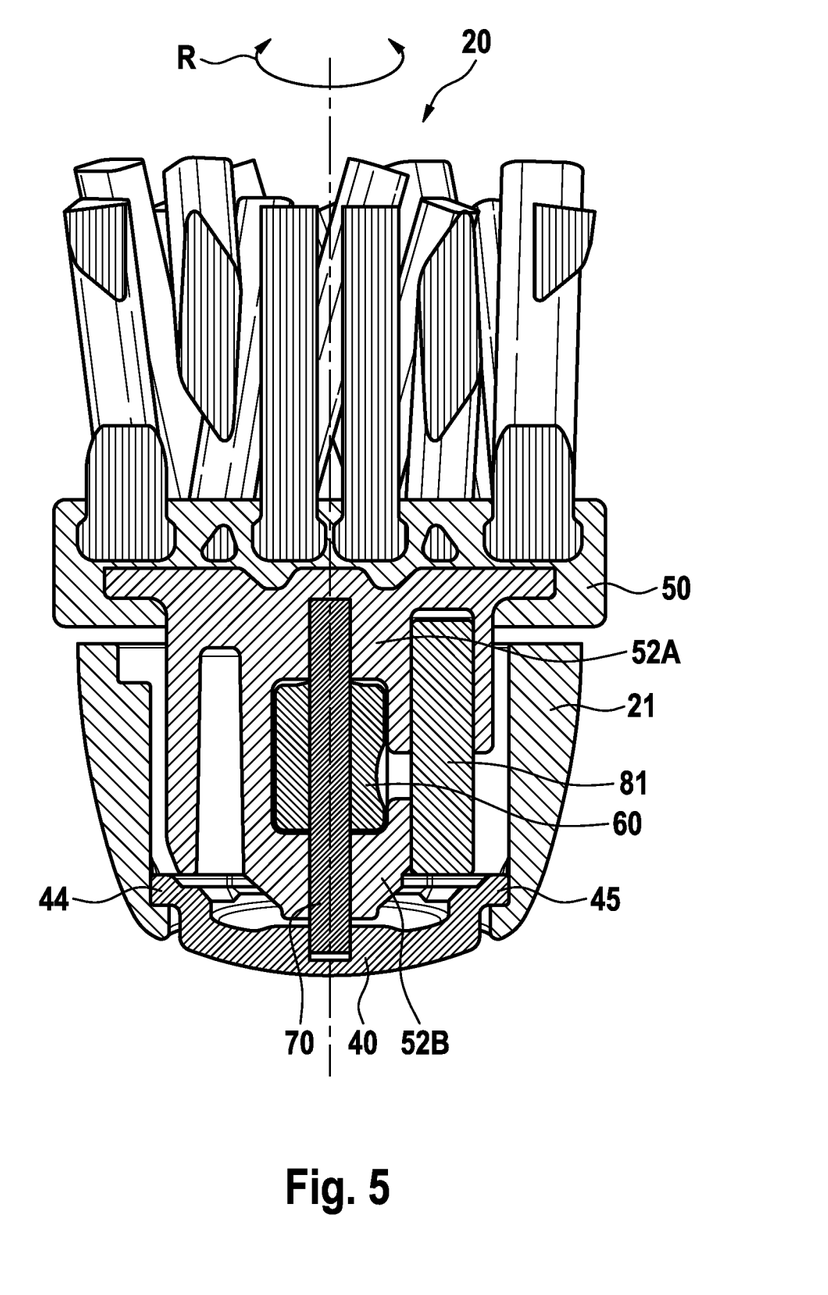
FIG. 5 is a cross-sectional cut through the oral hygiene implement shown in FIG. 2 taken through the plane as indicated by line D-D in FIG. 3.

FIG. 5 is a cross sectional cut through the oral hygiene implement 10 shown in FIG. 3 taken in a plane as indicated by line D-D in FIG. 3. In the shown embodiment, the cap element 40 has a third and a fourth connector structure 44 and 45 that cooperate with respective fixation structures (e.g. recesses provided in the inner side of the head section housing 21) provided on the inner side of the head section housing 21. The fixation structures may be defined by lateral side walls and at least a lower wall proximal the first opening 22A. In the shown embodiment, a cavity 52C formed in the mounting structure 52 of the carrier 50 is enveloped by the mounting sections 52A and 52B and the fixation element 60 is arranged in the cavity 52C so that the fixation element 60 (which itself is fixedly connected with the head section housing 21) locks the carrier element 50 against removal from the head section 20. A tappet 81 (that may be fixedly connected with the motion transmitter 80 shown in FIG. 4) may be arranged eccentrically with respect to the rotation axis R in a bore provided in the carrier element 50 to transfers a reciprocate linear movement that may be provided by the motion transmitter 80 (see FIG. 4—double arrow M) to the carrier element 50 so that the carrier element 50 oscillates around the rotation axis R defined by the axle 70.

FIG. 6 is a perspective depiction of an example embodiment of a cap element 40. The cap element 40 in accordance with the shown embodiment has a central cap structure 41 and may have four connector structures 42, 43, 44, and 45 for establishing a connection with the inner wall of the head section housing 21. In other embodiments, the cap element may have only one, two, three or more than four connector structures and the shown example embodiment is not to be interpreted as limiting (as stated above, in some embodiments, the cap element may no connector structure and may then, e.g., be interlocked via a fixation element). In the assembly process and with further reference to FIGS. 4 and 5, the cap element 40 may be inserted into the trough-hole 23 in the head section 20 via the second opening 22B. The second connector structure 43 may have two lateral wall segments 43A and 43B that are arranged to receive the axial projection 66 (see FIG. 4) of the fixation element 60 in-between them in order to define and fix the position of the fixation element 60. The cap element 40 additionally may have a support structure 49 for supporting and optionally also clamping the axle 70 (see FIG. 4). Further, the cap element 40 may additionally or alternatively have a circumferential flange 46 for improving the structural integrity of the cap element 40. The circumferential flange 46 may in particular be suited to guide forces and energy that may be transferred to the cap element 40 via the first connector structure 42 when the oral hygiene implement falls to the ground so that the energy and the forces are transferred via the second connector structure 43 to the head section housing 21 and to the neck section housing 31, where the energy and forces may be absorbed instead of plastically deforming and potentially fracturing the cap element 40, what may happen if a structural strengthening/force guiding element such as the circumferential flange 46 would be missing.

Figure 7:
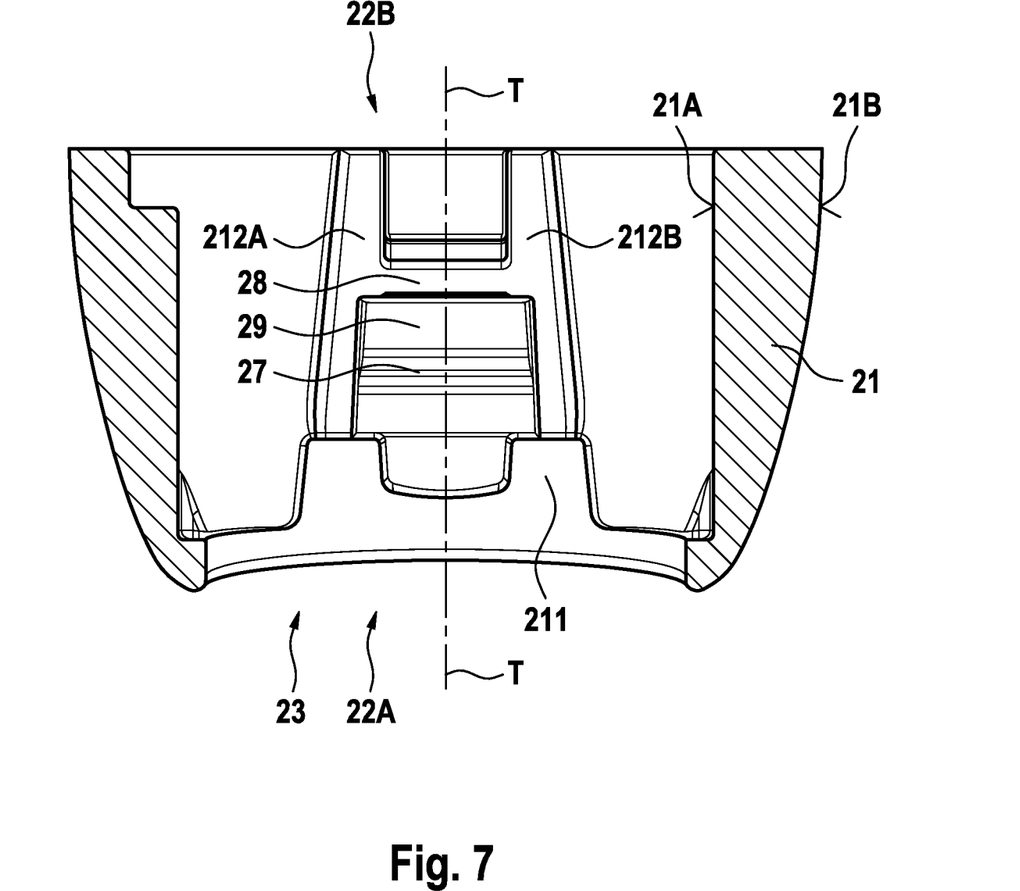
FIG. 7 is a cross-sectional cut along the same plane as in FIG. 5 but where only an example embodiment of a head section housing without the other parts of the head section is depicted.

FIG. 7 is a cross sectional cut through only the head section housing 21 shown along the same viewing direction as in FIG. 5 (i.e. towards the end of the head section distal to the neck section). The head section housing 21 has an inner side 21A and an outer side 21B. The through hole 23 defines the first opening 22A and the oppositely lying second opening 22B in the head section housing 21. The first projection 27 and the second projection 28 extend from the inner side 21A of the head section housing 21 radially into the through hole 23. The first and second projections 27, 28 are arranged on top of each other and with a distance with respect to the through-hole direction T. A depression 29 is arranged between the first and second projections 27, 28. Lateral side walls 212A and 212B are arranged laterally besides the first and second projections 27, 28 to guide and angularly position e.g. the cap element and/or the fixation element in the assembly process as already indicated. A U-shaped wall element 211 may be provided to receive and angularly and axially position a connector structure (e.g. the first connector structure 42 shown in FIGS. 4 and 6) of the cap element.

Figure 8:
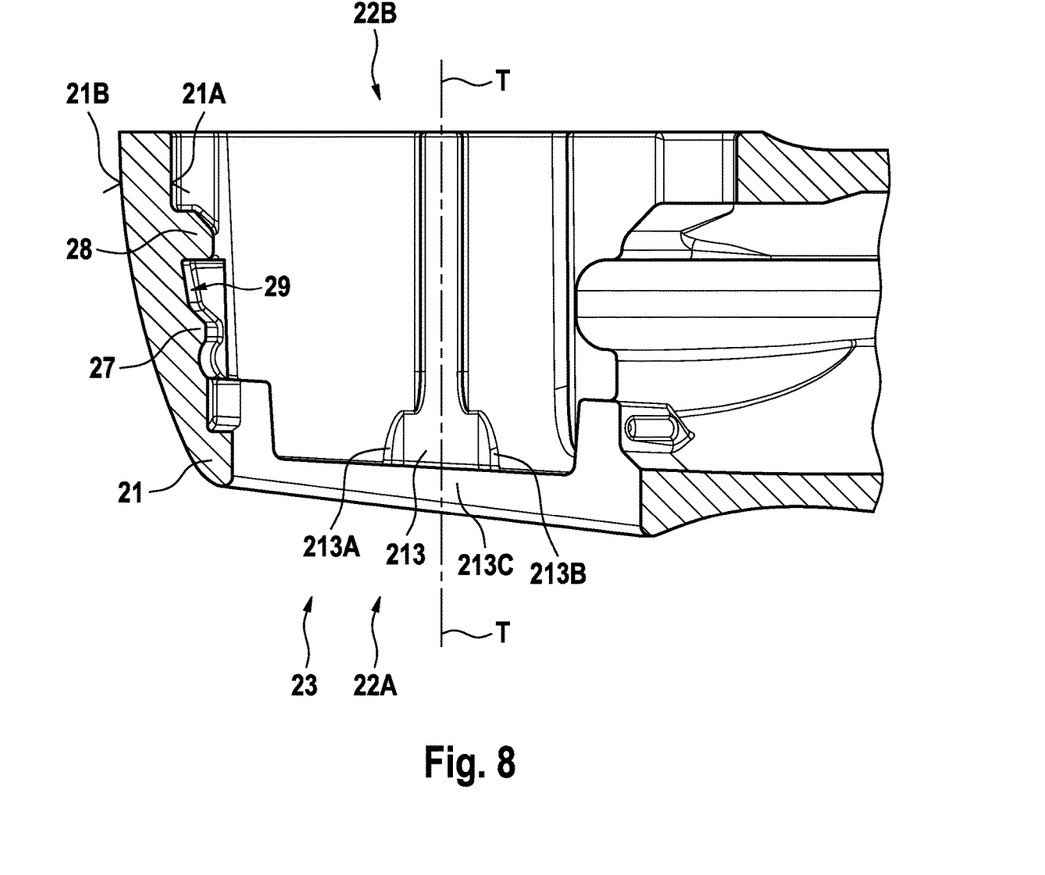
FIG. 8 is a cross-sectional cut along the same plane as in FIG. 4 but where only an example embodiment of a head section housing without the other parts of the head section is depicted.

FIG. 8 is a cross sectional cut through only the head section housing 21 shown along the same viewing direction as in FIG. 4. The head section housing 21 has an inner side 21A and an outer side 21B. The through hole 23 defines the first opening 22A and the second opening 22B in the head section housing 21. The first projection 27 and the second projection 28 radially extend from the inner side 21A of the head section housing 21 into the through hole 23. A first recess (or pouch) 213 is formed in the inner side 21A of the head section housing 21 that is defined by two lateral walls 213A and 213B and by a lower wall 213C, which first recess 213 may be provided to receive and angularly and axially position a connector structure of the cap element (e.g. the fourth connector structure 45 shown in FIGS. 5 and 6). A second recess may be provided in the inner side of the head section housing 21 just opposite to the first recess (e.g. to receive the third connector structure 44 shown in FIGS. 5 and 6).

Figure 9:
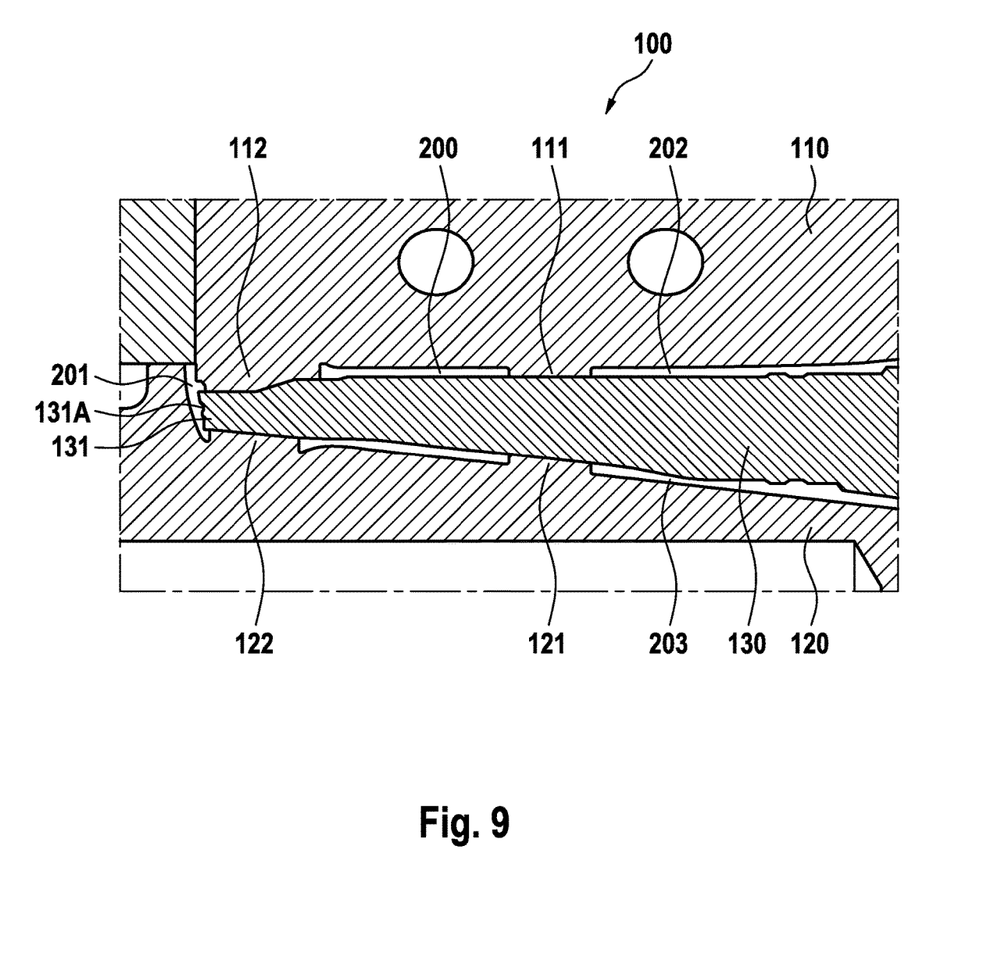
FIG. 9 is a schematic cross-sectional depiction of a detail of a mold by which steps of a method of manufacturing of an oral hygiene device in accordance with the disclosure can be realized.

FIG. 9 is a schematic cross-sectional depiction of a detail of a mold 100 for integrally injection molding of a head section housing and a neck section housing (together a housing part) of an oral hygiene implement in accordance with the present disclosure. The mold 100 comprises a first mold plate 110, a second mold plate 120 and a core 130, which three mold parts define a mold cavity 200 into which plastic material is to be injected to integrally form the head section housing and neck section housing. The core 130 defines the neck cavity, which essentially extends in a longitudinal direction from an end of the oral hygiene implement to the head cavity. The first mold plate 110 may comprise a first projection 111 projecting into the mold cavity 200 and the second mold plate 120 may comprise a second projection 112 projecting into the mold cavity 200 in order to fix and stabilize the core 130. In the shown example embodiment, the first mold plate 110 comprises a first shaping projection 112 and the second mold plate 120 comprises a second shaping projection 122, which first and second shaping projection 112, 122 are each in positive fit connection with a shaping front portion 131 of the core 130. Together, the first shaping projection 112, the second shaping projection 122, and the front shaping portion 131 define a through hole extending along a through-hole direction through the head section housing, the through hole defining a first and a second opening arranged opposite to each other in the head section housing. While the first shaping portion 112 and the second shaping portion 122 may also serve to further fix and stabilize the core 130, they also define portions of the shape of the inner side of the head section housing. Further, the shaping front portion 131 of the core 130 also defines a portion of the shape of the inner side of the head section housing. In particular, the shaping front portion 131 of the core may have at least one depression 131A to define a first projection radially extending from the inner side of the head section housing into the through hole, which first projection could otherwise not be ejected from the mold if the trough hole would, e.g. be only formed by two shaping projections of first and second mold plates 110, 120.

Generally, a housing part of an oral hygiene implement made by the above or other injection molding process and having two oppositely arranged first and second openings of a through hole in a head section of the housing part, may be subjected to a further injection molding process (either directly after the housing part has been made or after intermediate assembly steps), in which further injection molding step a cap element is formed that then essentially closes the first opening (a gap or holes may remain to allow, e.g., cleaning of the head section cavity).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:

1. An oral hygiene implement comprising:
a neck section extending along a longitudinal direction and having a neck section housing surrounding a neck section cavity;
a head section having a through hole therein extending through the head section along a through hole direction having an angle with respect to the longitudinal direction and having a head section housing surrounding the through hole;
wherein the through hole defines a first opening and a second opening in the head section housing; and
wherein a cap element separately made from the head section housing is connected with the head section housing to essentially cover the first opening and a carrier element separately made from the head section housing is arranged to essentially cover the second opening,
wherein the cap element is sized and configured to be inserted into the through hole from the second opening and towards the first opening, wherein the cap element has at least a first connector structure configured to engage a corresponding structure inside the through hole of the head section housing when the cap element is fixed from the inside to the head section housing to cover the second opening,
wherein at least a first projection being integral with the head section housing extends from an inner side of the head section housing into the through hole and at least a second projection being integral with the head section housing extends from an inner side of the head section housing into the through hole, the first and the second projections being arranged on top of each other and with a distance with respect to the through hole direction.

2. The oral hygiene implement in accordance with claim 1, wherein the cap element has been made in an injection molding process by which the cap element became connected with the head section housing.

3. The oral hygiene implement in accordance with claim 1, wherein a circumferential gap extends between an edge of the first opening and an edge of the cap element.

4. The oral hygiene implement in accordance with claim 1, wherein the cap element is made from a material that is different to the material from which the head section housing is made.

5. The oral hygiene implement in accordance with claim 1, wherein the cap element has a circumferential flange for structurally strengthening the cap element.

6. The oral hygiene implement in accordance with claim 1, wherein the carrier element is movably mounted at the head section.

7. The oral hygiene implement in accordance with claim 1, further comprising a fixation element that interlocks the cap element with respect to the head section housing.

8. The oral hygiene implement in accordance with claim 7, wherein the fixation element engages around at least one projection extending from an inner side of the head section housing into the through hole.

9. The oral hygiene implement in accordance with claim 1, wherein the cap element has an at least partly structured or textured outer surface.

10. An oral hygiene device comprising an oral hygiene implement detachably attached to a handle section, the oral hygiene implement comprising:
a neck section extending along a longitudinal direction and having a neck section housing surrounding a neck section cavity;
a head section having a through hole therein extending through the head section along a through hole direction having an angle with respect to the longitudinal direction and having a head section housing surrounding the through hole;
wherein the through hole defines a first opening and a second opening in the head section housing;
wherein a cap element is connected with the head section housing to essentially cover the first opening and a carrier element is arranged to essentially cover the second opening;
wherein the cap element is sized and configured to be inserted into the through hole from the second opening and towards the first opening, wherein the cap element has at least a first connector structure configured to engage a corresponding structure inside the through hole of the head section housing when the cap element is fixed from the inside to the head section housing to cover the second opening; and
wherein at least a first projection being integral with the head section housing extends from an inner side of the head section housing into the through hole and at least a second projection being integral with the head section housing extends from an inner side of the head section housing into the through hole, the first and the second projections being arranged on top of each other and with a distance with respect to the through hole direction.

11. The oral hygiene device according to claim 10, wherein the device is an electric toothbrush.

12. The oral hygiene device according to claim 10, wherein the carrier element is movably mounted on an axle such that the carrier element is adapted to rotate around a rotation axis defined by the axle.

13. The oral hygiene device according to claim 10, wherein the cap element is separably made from the head section housing.

14. The oral hygiene device according to claim 10, wherein the cap element is connected to the head section housing by injection molding.

15. An oral hygiene implement, comprising:
a neck section extending along a longitudinal direction and having a neck section housing surrounding a neck section cavity;
a head section having a through hole therein extending through the head section along a through hole direction having an angle with respect to the longitudinal direction and having a head section housing surrounding the through hole;
wherein the through hole defines a first opening and a second opening in the head section housing; and
wherein a cap element separately made from the head section housing is connected with the head section housing to essentially cover the first opening and a carrier element separately made from the head section housing is arranged to essentially cover the second opening,
wherein the cap element is sized and configured to be inserted into the through hole from the second opening and towards the first opening, wherein the cap element has at least a first connector structure configured to engage a corresponding structure inside the through hole of the head section housing when the cap element is fixed from the inside to the head section housing to cover the second opening,
wherein the at least a first connector structure comprises an outwardly extending projection structured and configured for a snapping engagement with a corresponding structure of the head section housing.

* * * * *